United States Patent [19]

Silbert

[11] 4,058,363

[45] Nov. 15, 1977

[54] METHOD AND APPARATUS FOR STERILE HANDLING OF FLUIDS

[76] Inventor: Jerome A. Silbert, 444 E. 84th St., New York, N.Y. 10028

[21] Appl. No.: 661,135

[22] Filed: Feb. 25, 1976

Related U.S. Application Data

[60] Division of Ser. No. 522,426, Nov. 11, 1974, Pat. No. 3,955,833, which is a continuation-in-part of Ser. No. 433,530, Jan. 15, 1974, abandoned.

[51] Int. Cl.² .............................................. A61L 9/00
[52] U.S. Cl. ..................................... 21/58; 128/214.2; 128/214 D; 137/15; 210/64; 210/501; 285/3
[58] Field of Search ............ 128/214 B, 214 D, 214.2; 21/58; 23/258.5 R, 253 R; 210/64, 321 B, 501; 285/3, 137 R, 150; 137/15

[56] References Cited

U.S. PATENT DOCUMENTS

| 3,211,144 | 10/1965 | Nehring ............................ 128/214 D |
|---|---|---|
| 3,282,775 | 11/1966 | Stonehill .......................... 424/333 X |
| 3,475,128 | 10/1969 | Thiers ........................ 23/258.5 R X |
| 3,753,493 | 8/1973 | Mellor .......................... 210/321 R X |
| 3,826,615 | 7/1974 | Smythe et al. ................ 23/253 R X |
| 3,902,489 | 9/1975 | Carter ........................... 128/214.2 X |
| 3,963,438 | 6/1976 | Banez ....................................... 21/58 |
| 3,986,508 | 10/1976 | Barrington .......................... 285/3 X |
| Re. 27,132 | 6/1971 | Ilg ................................... 23/258.5 R |

FOREIGN PATENT DOCUMENTS

| 737,249 | 6/1966 | Canada ........................... 128/214 R |
|---|---|---|
| 1,300,635 | 8/1969 | Germany ....................... 128/214 R |

*Primary Examiner*—Joseph Scovronek
*Assistant Examiner*—Arnold Turk
*Attorney, Agent, or Firm*—Bierman & Bierman

[57] ABSTRACT

Method and apparatus for sterile handling of fluids is provided, in particular blood, in which a manifold assembly having a plurality of ports or openings is connected to a fluid to be handled in sterile condition and to a sterilizing solution. The sterilizing solution is introduced into the manifold assembly preferably after the fluid unit is connected thereto so that all connections to the manifold are sterilized. The fluid is then permitted to flow into the manifold which is utilized to move it to one or more processing locations under sterile conditions.

33 Claims, 9 Drawing Figures

METHOD AND APPARATUS FOR STERILE HANDLING OF FLUIDS

The instant application is a Rule 60 Divisional application of co-pending Ser. No. 522,426 filed Nov. 11, 1974 which issued as U.S. Pat. No. 3,955,833 on May 11, 1976, which was a continuation-in-part application of then co-pending Ser. No. 433,530 filed Jan. 15, 1974, and now abandoned. The continuing priority of these applications is hereby claimed.

This invention relates to method and apparatus for the sterile handling of fluids and more particularly for the sterile processing of blood.

Today, blood collected for transfusion is being used rather inefficiently, with about 25% of blood collected from donors being lost through outdating. In this period of chronic shortages of blood for transfusions, it is vital to reduce waste of collected blood to an absolute minimum.

Another problem which has been plaguing medicine for years is the occurrence of post transfusion hepatitis which derives from the use of contaminated blood. Conservative studies have shown that about 17,000 post transfusion hepatitis cases occur per year along with about 850 deaths therefrom.

In an effort to increase the useful storage period of red blood cells, researchers in the field have found that red blood cells can be stored for 21 days if refrigerated. They further found that with glycerolization, red blood cells could be stored for 5 years if frozen.

In the processes of freezing and for washing red blood cells, the original blood unit is washed. For some reason currently not completely understood, hepatitis antigen is removed during washing to the point where the number of post transfusion infections and deaths from hepatitis can be significantly reduced, or eliminated as a major medical factor in blood transfusions.

To date, both government regulation and the high cost of washing red blood cells have militated against their use. The instant invention provides both method and apparatus for the sterile processing of blood at low cost to render economically feasible the washing of red blood cells and to make use of long term storage of blood components substantially free of hepatitis antigen. In addition, the washing of red blood cells under sterile conditions can reduce the level of other contaminants which can cause illness.

The fluid to which this invention relates can be any fluid which must be kept free from contamination during processing and during transfer from one point to another, including blood. The apparatus in accordance with this invention comprises a manifold having a plurality of openings through which the fluid is to be moved. Means are provided for connecting a container which contains the fluid, to the manifold. Preferably, the container for the fluid is sealed and, when inserted into the manifold, remains sealed. The means for connecting the container extend into the manifold and is exposed to a flow of sterilizing solution through the manifold. Processing appliances, such as centrifuges, may be connected to the manifold along with the fluid container so that all connections are exposed to the flow of the sterilizing solution.

In the preferred process, the sterilizing solution, which may consist of an alkalinized gluteraldehyde in 2% solution with or without the addition of a quaternary ammonium salt is moved through the manifold to sterilize its internal surfaces and the connection means of the various processing appliances and sterile fluid container. After sterilization is complete, a wash solution, such as a conventional saline solution, is then moved through the manifold to remove the sterilizing solution. At this point, the fluid container, which has been maintained in a sealed sterile condition, is broken to permit the fluid to enter the manifold. The fluid is moved through the manifold to a selected processing station, where a processing appliance, such as a centrifuge bag, is employed.

The sterilizing fluid not only sterilizes the interior of the manifold but also the connections from the various processing appliances which extend into the manifold, thereby assuring the sterility of the entire flow path between the interior of the fluid container and the processing appliance.

In a preferred form of apparatus, the means for connecting the fluid container to the manifold comprises a port which has a tube therein. The tube extends into the manifold and is covered with a membrane which is sterilized by the sterilizing solution. A connector, which is a part of the fluid container, is inserted into the port. The connector is provided with a needle having a bore therein in communication with the fluid. The connector itself is provided with a membrane which covers the needle and protects the interior of the connector from contamination until the membrane is broken.

When the connector is inserted into the port, the membrane covering the port is broken, thereby exposing a portion of the connector to the flow of sterilizing solution. After the sterilizing solution has been washed out of the manifold, the needle, which is moveable in the connector, is then moved to puncture the membrane sealing the connector to permit the fluid to flow into the manifold.

Although the particular connection and connector means described herein form a part of this invention, it is to be understood that any type of connection can be made to the manifold other than that described as long as the flow path of fluid is maintained sterile. In addition, sterilizing solutions other than alkalinized gluteraldehyde can be used depending on the nature of the fluid to be treated and the nature of the microorganisms to be destroyed. Also, washing solutions other than saline solutions may be used if desired. It would be well within the skill of the art to which this invention pertains to select appropriate sterilizing solutions for the particular purpose at hand.

The above-described method and apparatus can be used to process fluids in multiple units or in single units. In multi-unit processing, the continued sterility of the manifold and of the processing appliances must be assured. This can be done by sterilizing an entire manifold having a plurality of sections each of which is used for processing a single unit of liquid. After one section has been utilized, it is closed off from the remainder of the manifold. The process is repeated until all sections have been utilized. Alternatively, the manifold can be made reusable in either multi-unit or single unit processing by utilizing reclosable or self-sealing devices in the tubes and for connectors, such as membranes. Of course, the reclosable or self-sealing membranes should be resterilized each time a new unit of sterile fluid is to be processed.

The instant invention provides for the sterile transfer of fluids from a sterile container to another sterile processing appliance in a sterile environment. Whole blood or packed red blood cells are particularly adaptable to processing by the method and apparatus of this invention. Current regulation dictates that blood be stored for no more than 24 hours before use if the integrity of the container is breached. Component parts of blood can be stored for long periods of time depending on the treatment given. The present invention provides for sterile handling of the blood between container and processing appliance so that breaching the container does not expose the contents to contamination. The present invention provides sterile connections between the blood container and the processing apparatus which is quite simple in design and rather inexpensive, thereby making it economically feasible to transfer blood under sterile conditions for subsequent processing without worrying about additional contamination due to a breach of the original container.

This instant invention can also be used to process microorganisms or in connection with equipment designed to identify their nature and sensitivity. The apparatus of this invention, by providing a sterile path between the source of microorganism and the processing or identifying apparatus, can assure that the microorganism to be assayed is not contaminated by the transfer apparatus. Accordingly, the word "sterile" as used herein is to be construed to apply to the sterilization of the transfer apparatus for microorganism transfer as well as to the transfer of sterile fluids. The word "sterile" as used herein also means a degree of sterility needed to achieve the desired end result. Microorganisms may be permitted to remain which do not, or are not considered to be, contaminants of any significance. These and other aspects of the invention will become more apparent from the following detailed description taken in conjunction with the accompanying drawings.

Referring now to the drawings in which like numerals refer to like parts.

Figures 1, 2, 3, 4:
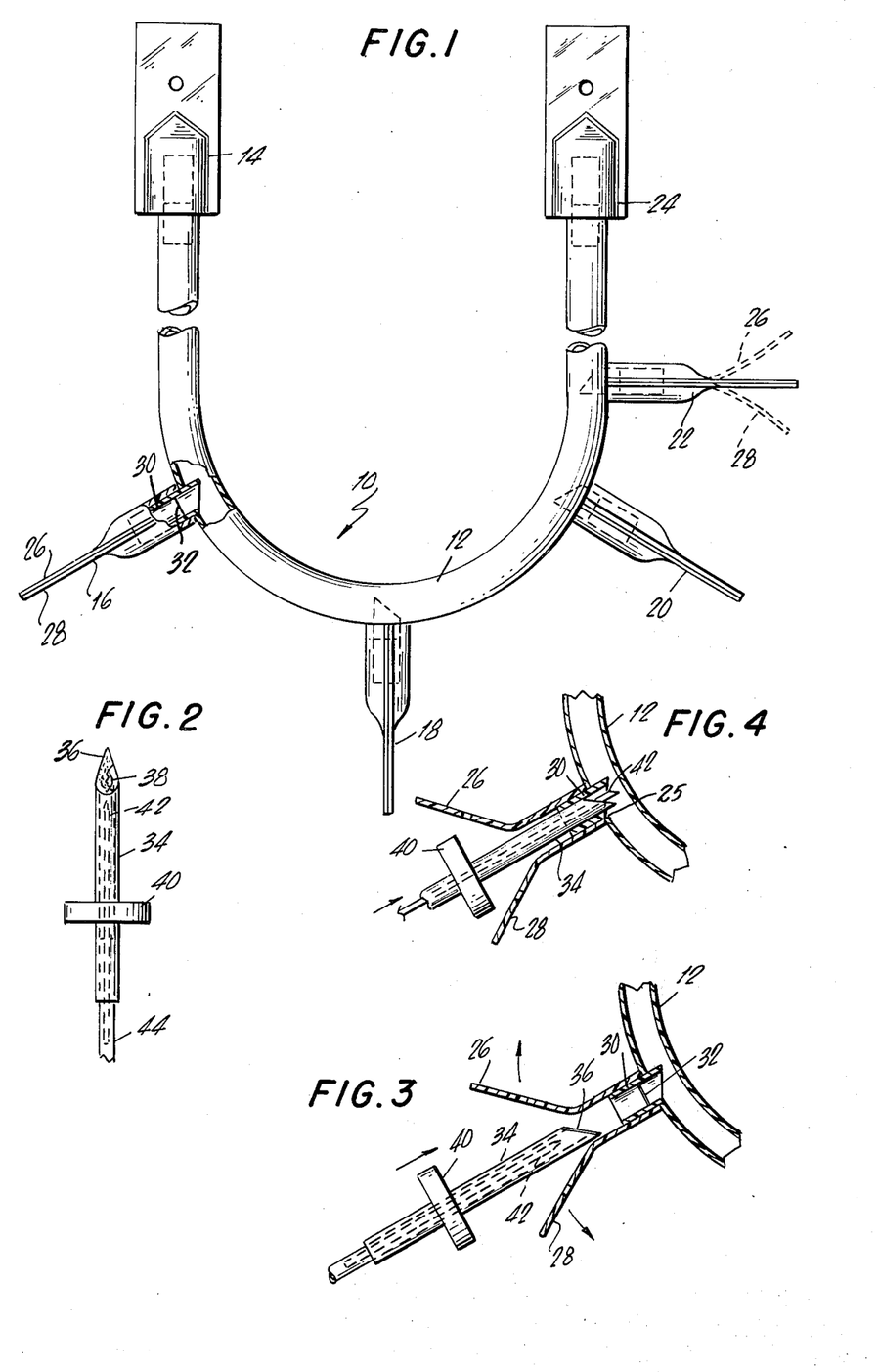
FIG. 1 is a plan view of a manifold used for single unit processing of sterile fluids.
FIG. 2 is a plan view of a connector useful in connection with the instant invention.
FIG. 3 is a plan view illustrating the step of inserting the connector into the manifold.
FIG. 4 is a plan view showing the connector after it has been inserted in the manifold.

Referring now to FIG. 1, the numeral 10 denotes a manifold assembly for the handling of fluids. The manifold tube is denoted by the numeral 12 and can be made from any material which will not react with the fluids to be moved through the manifold. For use with blood, polyvinyl chloride tubing is preferred.

A plurality of ports denoted by the numerals 14 through 24 are connected to the manifold 12. Ports 24 and 14 are, in this embodiment, connected to a sterilizing solution and to a effluent line respectively. The tab ports illustrated in FIG. 1 are all of the same construction.

The connection of the port to the manifold is most clearly indicated with reference to port 16 in FIG. 1 and to FIGS. 2, 3 and 4. The manifold 12 is provided with a plurality of openings 25 into which a small tube 30 is inserted. Tube 30 may be heat-sealed to the manifold or a non-reactive glue may be used to firmly anchor the tube 30 to the manifold 12. Preferably, the seal obtained between the tube 30 and the manifold is a hermetic seal. Surrounding tube 30 is a pair of tabs 26 and 28 which are flattened at the extreme edges adjacent tube 30 and which extend from the tube as a sealed unit. The rectangular area of ports 14 and 24 in FIG. 1 illustrate a plan view of tabs 26 and 28.

As illustrated in FIGS. 3 and 4, the tabs 26 and 28 can be moved apart to permit the insertion of a needle-like device generally indicated by the numeral 34.

Tube 30 has a forward end over which a sealing membrane 32 is placed. The sealing membrane 32 prevents the entry of contaminent to the interior of the manifold and also isolates the manifold interior from the external environment.

The needle-like device 34 comprises a barrel within which a hollow needle 42 is mounted. The interior of the connector 44, and the needle 42, are in communication via tubing 44 with either a sterile fluid container (not shown), microorganism source (not shown) or a processing appliance (not shown). The needle 42 may be friction-fitted within the hollow connector to prevent undesired movement of the needle. The hollow connector has an opening 38 which is covered by a membrane 36. The membrane 36 serves to isolate the interior of the hollow connector from the atmosphere. The hollow connector and the fluid container or processing appliance to which it is connected are preferably sterile. The internal sterility of the hollow connector and container are maintained by membrane 36 until the membrane is breached. If desired, a grip 40 may be placed on the hollow connector to make the connector easier to handle when it is inserted into the port.

Membranes 36 and 32 can be made from any material which is non-degradable in the presence of the fluids used in the manifold. When blood is to be processed, the membranes may be made of thin, flexible polyvinyl chloride secured to the tube 30 and to the connector 34. Cyclohexanone may be utilized in this instance as a glue to bond the membranes to their respective mating surfaces. By the same token, any material, including self-sealing rubbers and plastics can be used as long as they do not contaminate the interior of the manifold.

The operation of the apparatus shown in FIG. 1 will now be described in connection with the processing of a unit of blood. Initially, the container holding the blood will have a sterile hollow connector of the type shown in FIG. 2 mounted thereto. The tabs 26 and 28 of port 20 are peeled apart and the hollow connector inserted such that membrane 32 is punctured. During this phase of the process, membrane 36 remains intact. A sterilizing solution is introduced through tab port 24 into the manifold 12. The sterilizing solution bathes the entire manifold and is maintained in the manifold for a selected period of time necessary to destroy pathogenic microorganisms in the manifold. This is about 10 minutes for blood which can be reduced by the addition of a quaternary ammonium salt to the sterilizing solution. The sterilizing solution also bathes the tube 30 and the portion of the connector which has pierced membrane 32 so that all connections into the manifold interior are sterile.

In the embodiment of FIG. 1, a wash solution preferably a saline solution (not shown) is connected to port 22, fluid to be processed is connected to port 20 and a conventional "off" blood bag (not shown) is connected to port 16. All bags or appliances utilize connectors of the type shown in FIG. 2 and extend into the flow of sterilizing solution. As can be readily appreciated, all connections to the interior of the manifold for all processing steps are now sterile.

As sterilization is complete, tube 44 is closed to isolate the sterilizing solution from the manifold. At this point, the hollow needle associated with the wash solution is moved forward to break membrane 36. This can be achieved by bending tube 44 and pushing it against the end of the needle 42 in order to move the needle forward. At this point, the position of the needle is as shown in FIG. 4. The wash solution is then pumped by conventional means through the needle 42 into the manifold and is removed as effluent along with the sterilizing solution through port 14. The manifold is now ready for the processing of blood.

The needle associated with the unit of blood is then moved to pierce its associated membrane 36. At the same time, a processing appliance connected to port 18 is placed in communication with the interior of the manifold. The unit of blood flows to the processing appliance, which may be a centrifuge bag of the type shown in FIG. 10 commonly used for the separation of red blood cells from whole blood which process will be more fully described herein below. After centrifuging is complete, the "off" blood bag is connected to the manifold via the hollow needle associated therewith in order to remove the selected component of blood moved from the centrifuge bag into the manifold.

When processing blood, both gram negative and gram positive bacteria must be removed along with viruses, spores, etc. Gram negative bacteria and hepatitis antigens appear to be responsible for the most severe cases of post-transfusion infection and death. Gram positive bacteria, and other contaminants, although they can be responsible for post-transfusion infection, do not tend to cause infections as serious as gram negative bacteria and hepatitis antigens. An example of a microorganism which is rather resistant to normal sterilization methods are spores of gram positive bacteria.

As mentioned earlier, a preferred sterilization solution is alkalinized gluteraldehyde in 2% solution which is cidal against fungi, tuberculosis bacilli, viruses, spores and both gram positive and gram negative bacteria. However, the alkalinized gluteraldehyde is rather slow acting against spores. Although it is not deemed essential to increase activity against spores beyond that provided by the alkalinized gluteraldehyde, a quaternary ammonium salt can be added in a cidal amount to the sterilizing solution to increase the cidal activity of the sterilizing solution against the spores. The amount of the salt to be added is well known to those skilled in the art. As an alternative, the temperature of the sterilizing phase of the process may be increased to increase the cidal activity of the sterilizing solution.

As a wash solution, Elutralyte S-4, manufactured by the Fenwal Laboratories of Morton Grove, Illinois, can be used. However, it is to be noted that any sterilizing and wash solution, preferably saline and capable of yielding the degree of sterilization and washing desired can be used.

Figure 7:
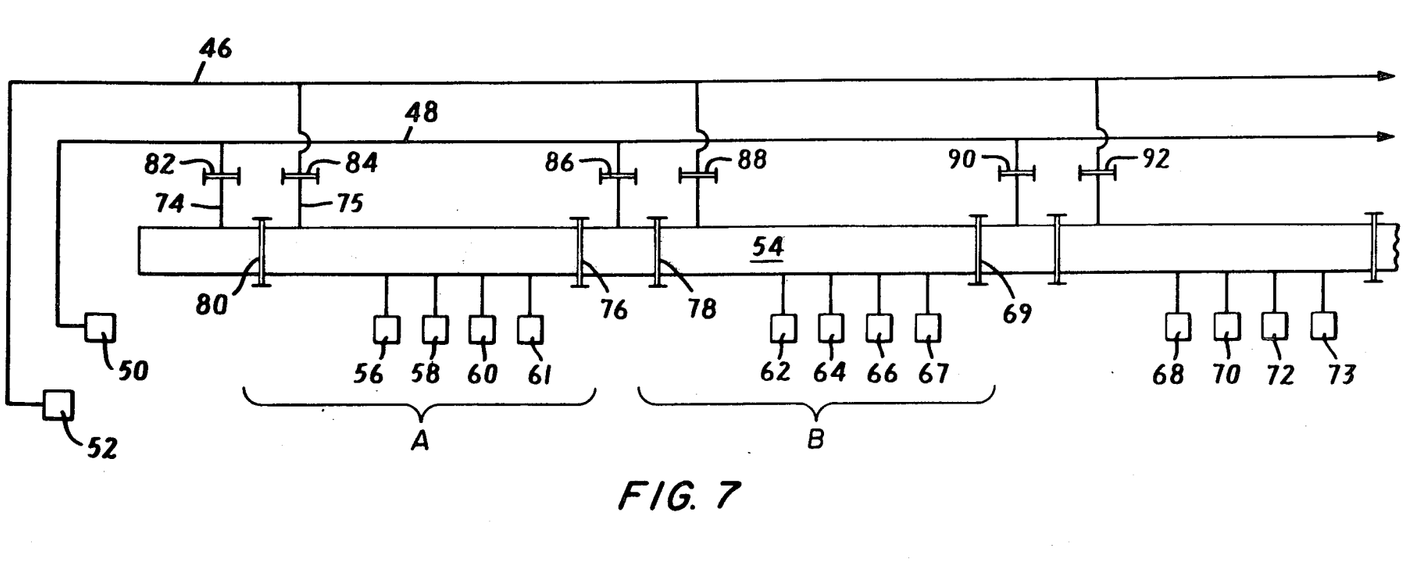
FIG. 7 is a schematic of a multi-unit processing apparatus.

FIG. 7 is a schematic layout of a multi-unit processing device. Line 46 and 48 represent manifolds similar to manifold 12 in FIG. 1. Manifold 48 is a feed line for sterilizing solution fed into manifold 48 from a container 50. Wash solution is fed into line 46 from a container 52. Container 50 may be connected to manifold 48 by the hollow connector and port assembly described in FIG. 1.

Container 52 is integrally connected to manifold 46. Manifolds 46 and 48 may be connected to Manifold 54 by the hollow needle connectors described in connection with FIGS. 1-4 to help assure the sterility of all connections into the main, or processing manifold 54.

Manifold 54 shown in the drawing is adapted to handle the sterile fluid to be processed. Numerals 56-73 are used to indicate either sterile fluid containers and/or processing appliances connected to the manifold through the use of sterile connectors and parts as shown in FIG. 1. The specific configurations of the connectors for connecting the processing appliances to the manifold are essentially the same as shown in FIGS. 1-4 for purposes of this description and have been omitted here for clarity.

In operation, sterilizing solution is introduced via reservoir 50 and enters manifold 54 through conduit 74. The sterilizing solution sterilizes the entire manifold 54. In the preferred process, clamps 82, 80, and 76 are then activated to isolate section A of the manifold 54 from the remaining sections. Wash solution 52 is then moved into the manifold through line 75 to cleanse Section A of sterilizing solution. Appliance 61 is in this instance used as an effluent line for the combined wash and sterilization solutions.

Assuming block numbered 56 to be a blood unit, the desired processing can now be carried out, via appliances 58 and 60. Since the manifold is preferably made of flexible polyvinyl chloride tubing, a conventional clamp can be used to isolate one part of the manifold from another.

During processing in Section A of the manifold, sterilizing solution is present in section B and in all remaining sections of the manifold 54. After processing is complete in section A, clamp 78 may be closed along with clamp 86, and clamp 88 opened to permit the introduction of wash solution to section B. Of course, clamp 69 is then closed to isolate section B from the remaining unused sections of manifold 54. The process described above is then repeated to process another unit of red blood cells and/or whole blood.

The entire process is repeated for as many sections as one has or cares to use along manifold 54. Of course, the clamps 88, 92 etc., controlling the input of wash solution to manifold 54 are normally closed, then opened to permit entry of wash solution to the section to be immediately used for processing, and then re-closed after washing, is complete. When red blood cells are to be washed, the wash solution may also be used to provide the saline solution generally used for such washing. Accordingly, the clamps controlling input of wash solution to the manifold 54 are then re-opened to permit entry of wash solution in the processing section being used.

Alternatively, the processing may be carried out by first introducing sterilizing solution throughout the entire manifold, and then washing the entire manifold prior to closing off the first section (section A).

In this alternative process, the same plurality of clamps 82 through 92 are shown for isolating the manifolds for feeding sterilizing and wash solutions to various portions of the manifold 54. As is readily apparent, clamp 80 will be closed after introduction of sterilizing solution and clamps 84 and 76 will be closed after wash solution has been flushed through the entire manifold. These clamps will remain closed throughout the subsequent processing of blood through the various sections of the manifold to maintain Section A isolated from the remainder of the manifold.

While section A is being used to process blood, section B is again subjected to sterilizing solution and subsequent washing to prepare section B for processing. Clamps 86 and 88 will be closed after sterilizing solution and wash solution have been admitted to manifold 54 in section B to resterilize that portion of the manifold containing processing appliances 62-73. This process is repeated for as many sections as one has connected to manifold 54.

Figure 8:
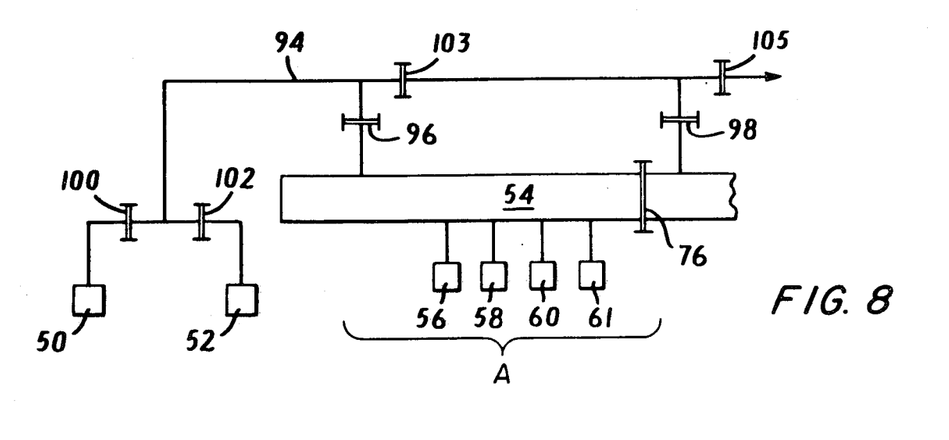
FIG. 8 is a partial schematic view of a modified apparatus of the type illustrated in FIG. 7.
Figure 9:
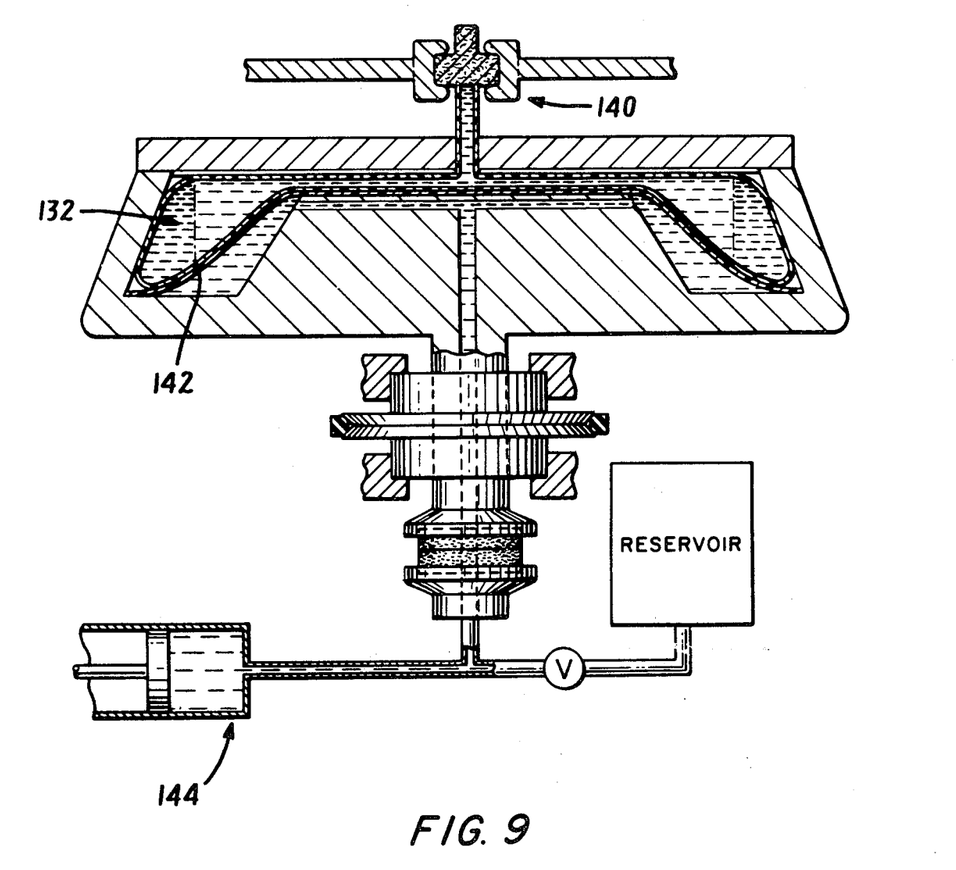
FIG. 9 is a plain view in detail of a centrifuge bag useful as a processing appliance in connection with the instant invention.

FIG. 8 shows an alternate form of apparatus in which sterilizing and wash solutions, indicated by numerals 50 and 52, respectively, alternatively feed a single manifold designated by numeral 94 in order to sterilize and wash the manifold 54. Clamps 96 and 98, 103 and 105 are shown for isolating various sections of the manifold after they have been used. The sterilization and wash solutions can be controlled through conventional clamps or valves 100 and 102 to permit either the sterilizing or wash fluid to enter the apparatus at the preselected time. Container 52 may be connected to manifold 94 via the connectors described in connection with FIGS. 1-4.

The multi-unit device described in FIGS. 7 and 8 allows reductions in processing time when multiple units of blood are to be processed. Since sterilizing solution is always present in sections of the multi-unit prior to processing that section, one eliminates the necessary residence time of the sterilizing solution as a factor in processing all blood units subsequent to the first one. This is achieved by leaving all clamps from the manifold to the sterilizing solution open until one is ready to wash out a particular section of the manifold. Clamp 103 is then closed along with clamp 76 and section A is then flushed out through effluent line 61, thereby readying section A for the processing of blood. When the next section is to be used, clamps 103 and 102 are opened and clamp 105 and clamp 69 (not shown) are closed to wash out section B through effluent line 67 (not shown). Alternatively, where the entire manifold is to be washed, clamps 100 and 102 are opened to wash solution to wash the entire manifold. After washing, clamp 96 and 76 are closed to isolate section A, and fresh sterilizing solution is permitted to flow into the remaining manifold sections, the process of washing then repeated. when it is desired to use the next section.

The apparatus illustrated and described herein can be used to wash red blood cells free of plasma. Specifically, FIG. 5 indicates a process for obtaining washed red blood cells from whole blood; and FIG. 6 is a flow chart for removing leucocytes from whole blood.

Figure 5:
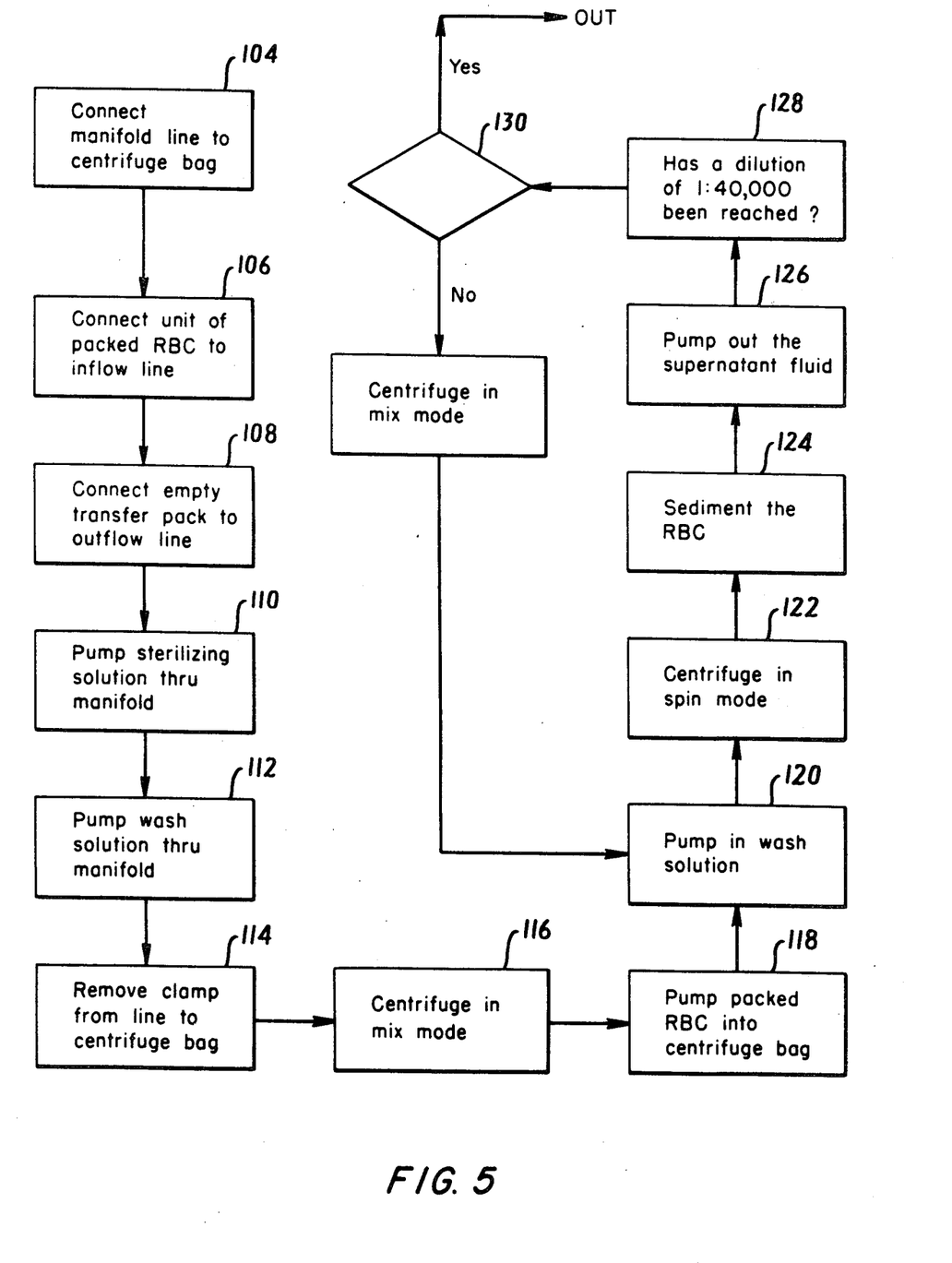
FIG. 5 is a flow chart illustrating the manner in which the single unit processing manifold is used for the production of red blood cells and plasma.
Figure 6:
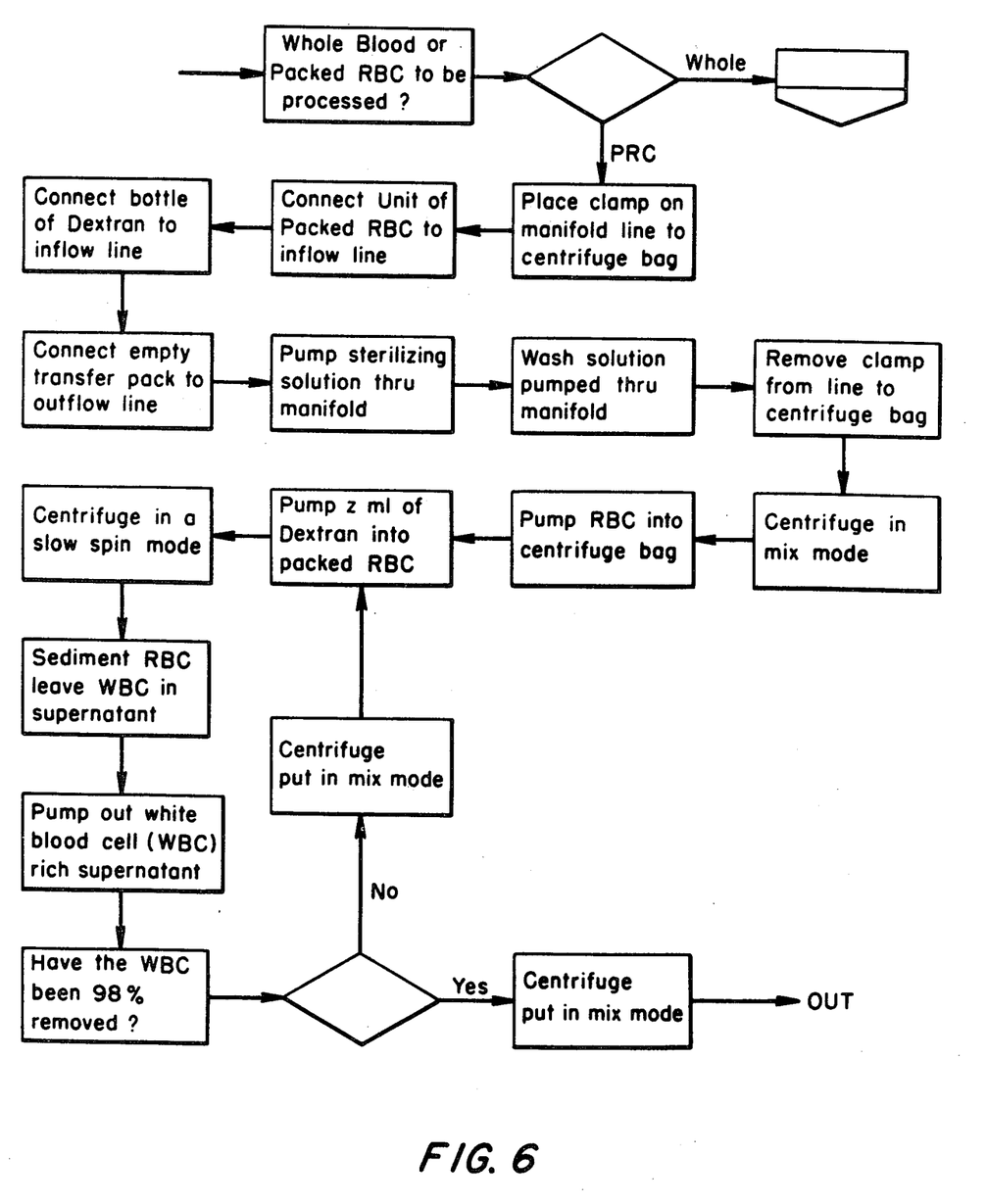
FIG. 6 is a flow chart illustrating the use of the single unit manifold for leucocyte removal.

Referring to FIG. 5, all process steps are indicated on the drawing. In block 104, the centrifuge bag or appliance is connected to the manifold via the connector illustrated in FIGS. 1-4 or any other suitable connector. Block 106 indicates that a unit of packed red blood cells is also connected to the manifold as well as an empty transfer pack as indicated in block 108. The centrifuge bag can be connected to port 18 in FIG. 1 and port 58 in FIG. 7. The unit of packed red blood cells can be connected to port 20 in FIG. 1 and to port 56 in FIG. 7. The empty transfer pack can be connected to port 16 in FIG. 1 and to port 60 in FIG. 7. Note that the effluent line can be connected to port 61 in FIG. 7.

As indicated in blocks 110 and 112, sterilization and washing of the manifold is then carried out such that all connections into the manifold are sterile. The centrifuge bag is then opened to the flow of packed red blood cells and the centrifuge operated as per blocks 114 and 116. The packed red blood cells are then pumped into the centrifuge bag along with wash solution which can be the wash solution from source 52, or from a separate source (not shown) which can be connected to the manifold through a separate port adjacent to the entry point of the red blood cells or of the processing appliance. These process steps are indicated in blocks 118 and 120. Blocks 122 and 124 indicate the steps needed to separate red blood cells from the resulting suspension. Blocks 126 and 128 indicate the steps necessary to remove the supernatent fluid which contains blood plasma. Preferably, a dilution of one in 40,000 for the blood plasma should be obtained as indicated in block 128. A dilution as low as this or lower tends to insure the absence of harmful microorganisms in the plasma. The wash cycle shown in blocks 120 through 128 is repeated a selected number of times until the appropriate dilution is obtained as indicated in block 130. This can be achieved by leaving the packed red blood cells in the centrifuge bag, pumping out the separated supernatent, and then adding fresh wash solution for each separate centrifuge cycle. It is estimated that about seven cycles are sufficient to fully wash red blood cells with the apparatus described herein.

A specific type of centrifuge bag is manufactured by IBM and shown in FIG. 10. The bag portion of the device is indicated by the numeral 132 and is disposable. The red blood cells along with wash solution are admitted through cover unit 140 into a position above an inflatable membrane 142. A hydraulic pump denoted by the numeral 144 pumps hydraulic fluid under the inflatable membrane which in turn can squeeze fluid out of the centrifuge bag while it is rotating in order to obtain separation between red blood cells and the supernatent liquid. The unit described in FIG. 10 is manufactured by IBM under the designation IBM 2991 Blood Cell Processor.

FIG. 6 is self-explanatory in view of the detailed description given for the process shown in the flow chart of FIG. 5. Those skilled in the art will be able to carry out any of the processes described in view of the detailed descriptions of apparatus and the explanation of methods contained in this specification.

In an experiment to determine the sterility of the manifold and connections made thereto, a device as shown in FIG. 1 was used in which sterilizing solution was introduced through port 22 after a bacterial solution had been introduced to the manifold through port 24. The bacteria used was a culture of Klebsiella species at a concentration of approximately one million colonies per ml. After moving the bacterial solution into and through the manifold, the manifold was clamped and a sterilizing solution moved into the manifold via port 22. The sterilizing solution consisted of a solution of 2% alkalinized gluteraldehyde. Several minutes were permitted to elapse and then a transfer pack containing thioglycollate culture broth and an empty transfer pack were connected to the manifold via the membrane covered couplers shown in FIGS. 1-4. At this point, additional sterilizing solution was run through the manifold and the manifold was then clamped below the sterilizing solution in-flow port 22. It is to be noted that the culture broth was connected through port 20 and the transfer pack through port 16.

After sterilization, the culture broth was opened into the manifold via its needle 42. The manifold was then clamped above the culture broth in-flow port 20. Some of the culture broth was then used to flush out the remaining sterilizing solution. At this point the transfer pack was opened into the manifold via its needle 42 and culture broth transferred thereto. The transfer pack and the culture broth collected at waste were then incubated at 37° C in excess of 2 weeks. No contamination was observed even though this particular bacterial species has a sticky mucoid surface, grows quickly, and is particularly difficult to remove.

Many modifications may be made in and to the above described apparatus and method by those skilled in the art. It is intended to cover all such modifications which fall within the spirit and scope of this invention as defined by the claims appended hereto.

What is claimed is:

1. Apparatus for the sterile handling of a fluid comprising: a manifold having a plurality of openings for the connection of various components thereto, isolating means for closing each of said openings and for maintaining the interior of said manifold sterile from the external environment, a plurality of separate hollow connecting members, mountable in said isolating means for projection into the interior of said manifold through said openings, each of said members having one end for connection to said components and its other end shaped for penetrating said isolating member, a seal at said other end of each of said members and means for breaking said seal, wherein said connecting members when mounted in said isolating means are movable between a first position in which said isolating means manintains the interior of said manifold isolated from the external environment and a second position in which the interior of the manifold is in communication with the said other end of said connecting members, and the seal on the other end of said connecting members maintaining the interior of said connecting members isolated from the interior of said manifold in said second position until said seal is broken.

2. The apparatus according to claim 1 wherein said isolating means further comprises a tube projecting into the interior of said manifold and having a tab which fits over one end of the tube, said tab normally maintaining the interior of the tube substantially isolated from the external environment.

3. The apparatus according to claim 1 wherein said isolating means comprises a tube projecting into the interior of said manifold and a closure mounted on said tube for keeping the interior of said manifold sterile from the external environment.

4. The apparatus according to claim 1 wherein said manifold is made of polyvinyl chloride.

5. The apparatus according to claim 1 wherein said seal in said connecting member is a puncturable membrane and said means for breaking said seal comprises a hollow needle means in each of said connecting members.

6. The apparatus according to claim 1 wherein the puncturable membrane mounted on said connecting members is a resealable membrane.

7. The apparatus according to claim 1 wherein said isolating means extends into the interior of the manifold and has a puncturable membrane mounted thereon in communication with the interior of the manifold, said connecting members not penetrating the membrane in said first position, and penetrating said membrane to expose the said other end of said connecting members to the interior of the manifold in said second position.

8. The apparatus according to claim 7 wherein said isolating means comprises a tube mounted in each of said openings with said puncturable membrane being in said tube.

9. The apparatus according to claim 7 wherein the puncturable membrane mounted on said isolating means is a resealable membrane.

10. The apparatus according to claim 1 wherein the fluid to be handled is blood and said apparatus is inert with respect to blood.

11. The apparatus according to claim 10 wherein there are at least five components connected to said manifold, the first being a blood container, the second being a sterilizing solution container, the third being a wash solution container, the fourth being an off bag for removal of blood from said manifold and the fifth being a blood-processing appliance.

12. The apparatus according to claim 11 wherein said processing appliance is a centrifuge bag.

13. The apparatus according to claim 12 wherein said manifold is divided into a plurality of processing sections, each said processing section having a plurality of isolating means thereon.

14. The apparatus according to claim 1 further comprising at least one additional manifold, having at least one component connected thereto, and means for joining said additional manifold to said first manifold at at least one connection point.

15. The apparatus according to claim 14 comprising a first component containing a sterilizing solution and a second component comprising a wash solution, said first and second components being connected to said additional manifold, and means for alternately permitting fluid from said first and second components to enter said additional manifold.

16. The apparatus according to claim 14 wherein said additional manifold is joined to the first manifold at a plurality of spaced points, and means for closing a portion of said first manifold to the entry of material carried in said additional manifold.

17. The apparatus according to claim 16 further comprising at least a second additional manifold having a component connected thereto, and means for joining said second additional manifold to said first manifold at at least one connection point.

18. The apparatus according to claim 16 wherein said means for closing are first clamp means on each means for joining to close the first manifold to the entry of material from said additional manifold.

19. The apparatus according to claim 18 wherein second clamp means are mounted on said first manifold adjacent each connection point to selectively isolate sections of the manifold from the remainder of the manifold.

20. The apparatus according to claim 16 wherein at least a second additional manifold is joined to said first manifold at a plurality of connection points adjacent the connection points at which said one additional manifold is joined to said first manifold.

21. The apparatus according to claim 20 further comprising third clamp means for selectively preventing flow of material from said second additional manifold to said first manifold through each individual connection point from said second additional manifold to said first manifold.

22. A method for the sterile handling of a sterile fluid in a container by an apparatus of the type having a sterile manifold normally sealed from the external environment comprising the steps of joining said container to one end of a sterile hollow connector having a sterile closure at the other end, inserting the closure end inside said manifold, forming a seal sterile from the external environment between said manifold and said closure end, introducing a sterilizing solution into said manifold, moving said sterilizing solution through said manifold to sterilize the interior of the manifold and the portion of said closure end exposed to the interior of said manifold, removing the sterilizing solution therefrom, breaking the closure and then moving the fluid into said manifold.

23. The method according to claim 22 wherein the step of removing the sterilizing solution from said manifold comprises moving a wash solution through said manifold.

24. The method according to claim 22 further comprising the steps of joining each of a plurality of sterile components to a sterile hollow connector and inserting each said connector into said manifold prior to sterilization so that all connections to said manifold are sterilized.

25. The method according to claim 24 wherein one of said components is a processing applicance wherein the fluid is agitated and comprising the step of moving said fluid from said manifold to said processing appliance for processing, then removing the processed fluid to said manifold, and then removing the processed fluid from said manifold.

26. The method according to claim 25 wherein said fluid contains packed red blood cells.

27. The method according to claim 25 wherein the steps of moving said fluid to a processing appliance comprises moving said blood in said manifold to a centrifuge bag, centrifuging the blood, and then returning at least a portion of the centrifuged blood to said manifold, all under sterile conditions.

28. The method according to claim 25 wherein said fluid is whole blood.

29. The method according to claim 28 wherein said sterilizing solution is alkalinized gluteraldehyde in 2% solution and wherein the step of sterilizing comprises the step of maintaining said sterilizing solution in said manifold for a sterilizing period.

30. The method according to claim 29 wherein said sterilizing solution has a quaternary ammonium salt added thereto in a sterilizing amount.

31. A method for transferring multiple units of blood to be processed comprising the steps of providing a first manifold having a plurality of sections for the sterile transfer of blood for the processing of individual units thereof, joining at least one container having a unit of blood therein to one end of a sterile hollow connector having a sterile closure at the other end, inserting said closure end inside a first section of said manifold forming a seal sterile from the outside environment between the manifold and said connector and maintaining said blood sealed off from said manifold, moving sterilizing solution through said manifold to sterilize the interior of the manifold and the portion of said closure end exposed to the interior of the manifold, and removing said sterilizing solution from at least the first section of said manifold isolating the first section of said manifold from other sections, breaking said closure and moving said blood into the sterile first section, and maintaining said first section isolated from other sections of said manifold during transfer of blood units in said other sections.

32. The method according to claim 31 wherein the steps of isolating and removing comprise the steps of isolating a first section of the manifold after sterilizing solution has been introduced to said manifold and permitting sterilizing solution to remain in said other sections.

33. The method according to claim 31 wherein the step of removing the sterilizing solution from said manifold comprises moving a wash solution through said manifold.

* * * * *